(12) United States Patent
Wise

(10) Patent No.: US 10,147,258 B2
(45) Date of Patent: Dec. 4, 2018

(54) SYSTEM FOR CROWDFUNDING AND CROWDSOURCING COMPETITION

(71) Applicant: Kelley Wise, Villa Park, CA (US)

(72) Inventor: Kelley Wise, Villa Park, CA (US)

(*) Notice: Subject to any disclaimer, the term of this patent is extended or adjusted under 35 U.S.C. 154(b) by 0 days.

(21) Appl. No.: 15/046,230

(22) Filed: Feb. 17, 2016

(65) Prior Publication Data

US 2016/0240026 A1 Aug. 18, 2016

Related U.S. Application Data

(60) Continuation-in-part of application No. 14/154,108, filed on Jan. 13, 2014, now Pat. No. 9,384,365, which is a division of application No. 13/465,789, filed on May 7, 2012, now Pat. No. 8,631,506, which is a division of application No. 12/723,283, filed on Mar. 12, 2010, now Pat. No. 8,195,937, which is a division of application No. 11/625,072, filed on Jan. 19, 2007, now Pat. No. 7,685,417.

(51) Int. Cl.
| | |
|---|---|
| G06F 21/53 | (2013.01) |
| G07C 13/00 | (2006.01) |
| H04L 29/06 | (2006.01) |
| H04L 29/08 | (2006.01) |
| G06Q 30/02 | (2012.01) |
| G06Q 30/04 | (2012.01) |
| G06F 19/00 | (2018.01) |
| G06F 21/62 | (2013.01) |
| G06Q 50/00 | (2012.01) |

(52) U.S. Cl.
CPC ............ *G07C 13/00* (2013.01); *G06F 19/321* (2013.01); *G06F 21/53* (2013.01); *G06F 21/6245* (2013.01); *G06Q 30/0279* (2013.01); *G06Q 30/04* (2013.01); *G06Q 50/01* (2013.01); *H04L 65/60* (2013.01); *H04L 67/18* (2013.01); *G06F 2221/032* (2013.01); *G06F 2221/2149* (2013.01)

(58) Field of Classification Search
CPC ...................................................... H04L 65/60
See application file for complete search history.

(56) References Cited

U.S. PATENT DOCUMENTS

| | | | |
|---|---|---|---|
| 2009/0187936 A1* | 7/2009 | Parekh | H04H 20/38 725/25 |
| 2014/0280231 A1* | 9/2014 | Paruchuri | G06F 17/30038 707/749 |

* cited by examiner

*Primary Examiner* — Josnel Jeudy
(74) *Attorney, Agent, or Firm* — Niro McAndrews, LLP

(57) ABSTRACT

Apparatus and methods concerning a crowd sourced database of content featuring content uploaded for the purpose of achieving a desired outcome for the contributing user and using a user based voting system for an established duration that is limited to established geographical areas and allows users to vote for contributing users to go from a starting page to a state page and up to a national page for the purpose of awarding a prize or other desired outcome to the contributing user by winning the most votes on a national level. The contributing user may pay a fee per state to be included in that state's voting process.

9 Claims, 2 Drawing Sheets

SYSTEM FOR CROWDFUNDING AND CROWDSOURCING COMPETITION

This application is a continuation-in-part of U.S. patent application Ser. No. 14/154,108 that was filed on Jan. 13, 2013 that was a divisional application of U.S. patent application Ser. No. 13/465,789 filed on May 7, 2012 that was a divisional of U.S. patent application Ser. No. 12/723,283 filed on Mar. 12, 2010 that was a divisional of U.S. patent application Ser. No. 11/625,072 that was filed on Jan. 19, 2007.

BRIEF DESCRIPTION OF THE INVENTION

In our novel system for a profitable crowd sourced content database "application service provider" ("ASP"), the ASP provides streamed videos, web pages, television shows, and other media and or content to users with the ASP's App installed on their smart phone or computers or as a zero footprint App, to view contributed content and thus are enable to view a wide number of offerings in the form of the contributed content and make investments or vote for any stated outcome desired by the contributed content and to allow users to create a funding campaign or enter into a contest or compete to achieve a desirable outcome for their stated desired outcome to be streamed and displayed in an App with a video or web page or show or performance in any medium displayed in the App and or other similar media platform for an established amount of time and limited to an established geographic area. Any viewer of the contributed content or data set uploaded by the user or contestant must register into the ASP as a user and is bound to the rules of the ASP by the functions of the App provided by the ASP and its server so the user may place one vote per voting period set by the established amount of time and other established parameters or categories of desired outcomes sought by the contributing users or contestants. The apparatus applies metadata to the contributed content to identify the user and their geographic location, and other relevant meta data to provide controls over the display of the contributed data and the geographic area a user may vote for a contribution and other meta data signifiers which allows the apparatus to establish parameters of access to the data according to the function of the apparatus defined herein. Since the votes for each contributing user's campaign, web page or content uploaded is limited to just their own state for everyone, and voters can only vote for content shown on their states voting site, the uploading user or contestant may improve their odds of being voted to the state and then national level by paying a fee to be featured on one or more or all fifty U.S. States and receive votes in every state served by the ASP. The winner of the most votes on the national portal, web site, or show receives the money or prize or whatever the stated desired outcome is depicted in the user's uploaded contribution.

A streaming application service provider ("ASP") is capable of performing services and provide a level of interaction with a large number of users over such a wide scale that many businesses and most all people now rely on their smart phones and other Internet connected computer controlled device to accomplish numerous operation that are not possible any other way to deliver the same speed and scope of operation without a cloud based App provided by an application service provider for that purpose. Most Apps are business models that can only be executed online and by streaming content to a user's smart phone or computer or computer controlled device. Streaming data sets with identifying metadata allows the metadata to provide a set of rules for the server that streams the data and the viewer or App the displays the data and sets the rules for the user to interact with the data in a dynamic manner. Performing the decoding and interaction with the data in a virtual machine or similar browser based viewer apparatus the system can function on a smartphone as an App. Streaming content and data to a smartphone or A crowd funding site funds projects by users soliciting donations or investment for their project, business, charity, idea, other such need on an individual basis where the requests for funding and the promotion of these requests and their associated web pages and content accessed through an app or zero foot print viewer with a smartphone or other computer enabled device, can be considered contributions to a crowd sourced database which generated crowd sourced investments and cash contributions to these users based on their uploaded content contributions. Our novel method can fund a project, candidate, charity, or any other purpose or person on a much larger scale than otherwise possible by incorporated our novel method of a pay to be seen voting competition where only the winner takes the prize which could be cash, a prize, a lucrative contract, a job, or any other type of desirable objective for any type of purpose like a charity or a business venture or a movie deal, invention, in fact anything that needs to be funded or can be decided or chosen by this apparatus and method of regulated online voting using metadata attached to the streamed contributed content of a crowd sourced database, and geographic region of the logged in voting user which the app identifies and uses to regulate the voting regions of the voting user.

A present embodiment of this invention does not provide the contributing user to the content database which seeks to increase their odds of being seen by more viewers than a competitor or for the contributed content or data sets to be voted to the top of the list for a wider audience or to access an apparatus that offers a better chance of winning a contest. These embodiments only have a passive method and apparatus to generate more views which generate investments or cash contributions to their stated desired outcome, or getting the most votes to achieve any established result. The operator of the crowd sourced content database has only ad sales for each view of each crowd sourced content contribution. In our novel system for a profitable crowd sourced content database "application service provider" ("ASP"), the ASP provides videos, web pages, television shows, and other media outlets to allow users to create a funding campaign or enter into a contest or compete to achieve a desirable outcome for their stated desired outcome displayed on the video or web page or show or other similar media platform for an established amount of time and limited to an established geographic area. Any viewer of the contributed content or data set uploaded by the user or contestant must register into the ASP as a user and is bound to the rules of the ASP by the functions of the App provided by the ASP and its server so the user may place one vote per voting period set by the established amount of time and other established parameters or categories of desired outcomes sought by the contributing users or contestants. Since the votes for each contributing user's campaign, web page or content uploaded is limited to just their own state for everyone, and voters can only vote for content shown on their states voting site, the uploading user or contestant may improve their odds of being voted to the state and then national level by paying a fee to be featured on one or more or all fifty U.S. States and receive votes in every state served by the ASP. The winner of the most votes on the national portal, web site, or show receives the money or prize or whatever the stated desired outcome is depicted in the user's uploaded contribution. The system allows for the creation of many different genres participating and sub-genres that create even more participation. In situations where genres that are very small the population groupings could cover the whole east coast of west coast or any different possible population grouping can be made according to the size of the genre of content to fit the required critical mass of population size to make the system economically feasible for every genre or funding requirement, and every possible campaign under this method and apparatus. The Meta data tags applied to each data set will have parameters established on the file to prevent the content from being uploaded to a campaign that cannot achieve the desired outcome attached to the uploaded content from the contributing user.

This is a far more profitable business model for the ASP than just selling banner ads and other advertising which are paid on a per view basis. Depending on the use of the method apparatus of my novel invention, the ASP could sell banner ads and other types of per view or per click models of ad sales, and also monetize the ASP by selling contributing users the right to get votes for their contributed content or data sets in other states on a per state basis and provide the winners of each voting cycle in each established category of contests or funding requests or other such use of the apparatus a much larger amount of money or prize or investment or other such desired outcome than would otherwise be possible using the present embodiment of the invention.

DETAILED DESCRIPTION

Figure 1:
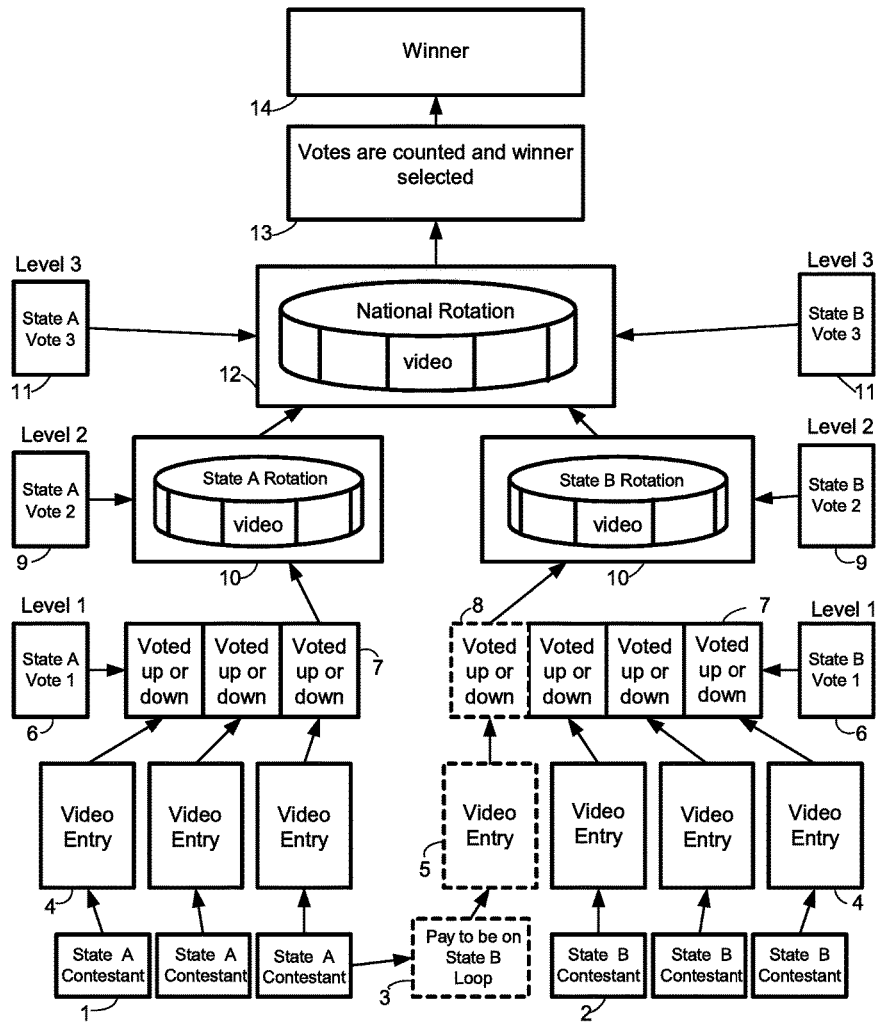
FIG. 1 shows a representation of the method and apparatus of aggregating content to a crowd sourced content database for the purpose of giving contestants or content contributors a method to go from having no promotion of the contributed content, to having state level promotion and national promotion; to receive votes from users that view the contributed content for the purpose of being advanced to higher levels of competition or wider exposure or rotation of a pitch, campaign, advertisement, web page, video or music or other medium, shown or played on a loop or other format at a state level and on a national level in order to be voted as the winner or recipient of the prize and or stated desired outcome; and providing an apparatus for the contributing user to pay a fee to be able to receive votes from users in other states beyond their own state for which the apparatus restricts their ability to vote beyond contestants or contributing users located in their own state. The winner of the most votes on the national level receives their stated desired outcome.
Figure 2:
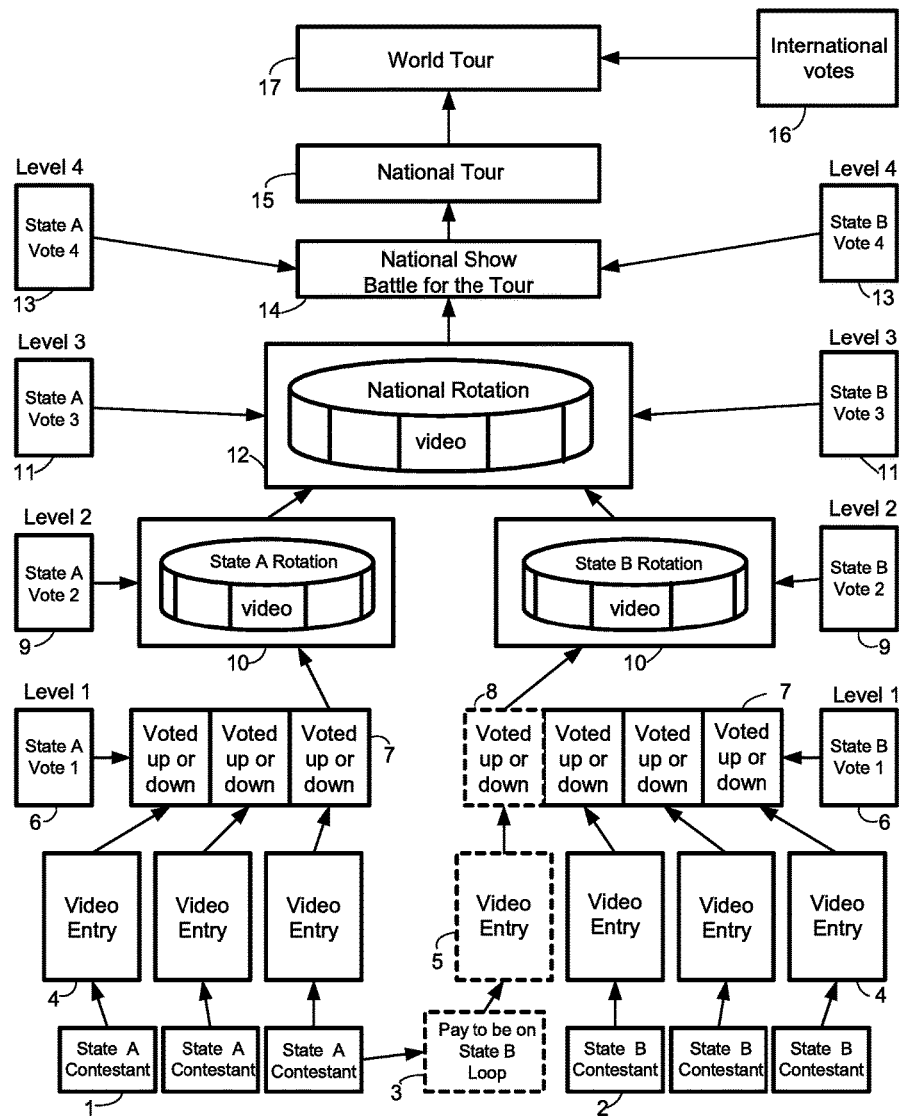
FIG. 2 shows a representation of the method and apparatus of aggregating content to a crowd sourced content database for the purpose of giving contestants or content contributors of music or entertainment performances and other content a method to go from having no promotion of the contributed content, to having state level promotion and national promotion; to receive votes from users that view the contributed content for the purpose of being advanced to higher levels of competition or wider exposure or rotation of a video or music shown or played on a loop or other format at a state level and on a national level in order to be voted as the winner or recipient of the prize and or stated desired outcome; and providing an apparatus for the contributing user to pay a fee to be able to receive votes from users in other states beyond their own state for which the apparatus restricts their ability to vote beyond contestants or contributing users located in their own state. The winner of each voting round goes on to perform on a show and can receive votes again at this level to go on a national tour and world tour.

My novel method and apparatus for a profitable crowd sourced content database and or online talent contest and or crowdfunding apparatus uses an App or a zero foot print viewer or user interface as a component or apparatus of an "application service provider" ("ASP"), the ASP provides access to the service through a web site or App. A Contributing User (1) that contributes content into the ASP could be among other things, a band, DJ, comedian, singer, short film maker, visual artist, and performer or artist of any kind, or anyone or any company or any organization or charity or group could use the method and apparatus to attempt to be voted the winner/s of an established a prize or cash award, or investment, or contract, movie deal, or any other desired outcome for an established duration of time by logging in and becoming contestants (1) to be allowed to upload any type content (4) performance on video or audio, or images and presentation of any type (4); for entry into an online contest where users from each state, shown in the diagram as two states, state A contestant (1) and state B contestant, (2) have one vote in each voting cycle, per level to be cast on only one specific user's contributed content per voting cycle, to decide which contributed content in the database moves from a starting location on the App for each contributing user; which is established as being made in an established geographic location and limited to only votes that location (7); and is voted up (7) to a state level of rotation (10), promotion, and voting competition by voters from the same state (10). The contributing users have their videos or other type of presentation as rotating content or highlighted content or featured content in a level of the App or contest as representative of the state the content where the contributing user is registered by the App (10). Streaming data sets with identifying metadata allows the metadata to provide a set of rules for the server that streams the data and the viewer or App the displays the data and sets the rules for the user to interact with the data in a dynamic manner. Performing the decoding and interaction with the data in a virtual machine or similar browser based viewer apparatus the system will only function on a smartphone as or computer enabled device as an App. My novel method enables this apparatus to permit a contributing user to pay a fee (3) to the ASP to have their contributed content uploaded to content that is attributed to the state other than the contributing user's own state (5) they would otherwise be limited to upload to for voting purposes. The paid contributed content (5) is now eligible for voting in other states (8) and can be voted by those state user voters (6) up to that state's statewide rotation (10) of the most popular contributed content or data sets. Users at each state (9) may vote once during each campaign for any category of content in rotation on the state level contributed to the content database (10) to participate in letting the ASP using its App to select a winner or winners of each category of contest at the state level to advance to the national level (12) where all user voters (11) from every state may vote on the winner or winners of the contest (13), and the established prize or prizes are awarded (14).

The contributed content may be displayed as a recorded message, a song, movie clip, short film, video, popular performances, or any other type of streamed data sets featured for access or showing on a loop and promoted on the ASP's entertainment website or other manner of method of streamed media presentation of content. The content can be any form of online communication medium which can be streamed to a virtual machine component operating on a smart phone or computer enabled device. Each state has its own contest entry portal on the App. Contestants may only create a channel in the state they register as residing in, and the channels may only be viewed by Apps that the system identifies as being in the same state. Users access the ASP through an App which only provides access to the contestant's video channels which were made in their own state to view. The App also provides users access to streamed video or data which received enough votes to move a song, video or other type of streamed content into prominent display and highest on the online popularity chart, and rotation on a loop of featured streamed entertainment such as video and other online content. Users view videos on contestant created channels as much as they like and vote contestants may log into and view videos provided by the contestants. A campaign can be any length of time, such as a month, a week, an hour, or a day.

The ASP ("ASP") provides streamed videos, web pages, television shows, and other media and or content to users with the ASP's App installed on their smart phone or computers or as a zero footprint App, to view contributed content and thus are enable to view a wide number of offerings in the form of the contributed content and make investments or vote for any stated outcome desired by the contributed content and to allow users to create a funding campaign or enter into a contest or compete to achieve a desirable outcome for their stated desired outcome to be streamed and displayed in an App with a video or web page or show or performance in any medium displayed in the App and or other similar media platform for an established amount of time and limited to an established geographic area. Any viewer of the contributed content or data set uploaded by the user or contestant must register into the ASP as a user and is bound to the rules of the ASP by the functions of the App provided by the ASP and its server so the user may place one vote per voting period set by the established amount of time and other established parameters or categories of desired outcomes sought by the contributing users or contestants. In another embodiment of the invention the ASP can also break up the state votes into population zones based on the size of the given population for instances where a large state would overwhelm smaller states in content creation and voters. This will help eliminate unfair advantages which may harm the odds of users in large states users in small states. Other variations of the population grouping can be made according to each type of content and genre of the content in order to achieve the desired outcomes because this method and apparatus is adaptable to any scenario because the apparatus and method do not change when applied to each different category of applications of the invention and can be replicated and expanded to cover a myriad of different variations of contributed content and the desired objectives or outcomes. Contributing users may also pay the ASP for additional spots on the rotation once they have made it onto the statewide or national rotation, creating addition revenue for the ASP using this method and apparatus. Contributing users can also pay the ASP for promo ads on the state and national rotation sites once they have reached those levels. The Meta tag content controls can be dynamically changed by the SP for each different type of campaign as required to control and establish the parameters and rules and duration and all the other factors for each campaign in this manner and maintain the integrity of the system form hackers and tampering.

The apparatus applies metadata to the contributed content (4) to identify the user and their geographic location, and other relevant meta data to provide controls over the display of the contributed data and the geographic area a user may vote for a contribution and other meta data signifiers which allows the apparatus to establish parameters of access to the data according to the function of the apparatus defined herein. Since the votes for each contributing user's campaign, web page or content uploaded is limited to just their own state for everyone, and voters can only vote for content shown on their states voting site, the uploading user (1) or contestant may improve their odds of being voted to the state and then national level by paying a fee (3) to be featured on one or more or all fifty U.S. States and receive votes in every state served by the ASP. The winner of the most votes on the national portal, web site, or show receives the money or prize or whatever the stated desired outcome is depicted in the user's uploaded contribution (14). To add more rotation or qualifying indicated using Meta tag and Meta data applied to each uploaded data set, the apparatus can be automated in manner to allow the database to dynamically move file with established metadata parameter imprinted on the data the crowd sourced data base can dynamically place the uploaded content in the appropriate location. This method assures integrity to the system by streaming the data in an encoded format which is not downloadable in its intent because it streams to a virtual execution environment inside a buffer and logically independent of the user's smart phone or computer, computer, or enabled device. In another embodiment of the invention this method can also allow the remote user to access established features on the content that the Meta data enable on the remote viewer App on the smart phone, computer, or computer enabled device.

This method can be applied to broadcast television if a smart phone of computer enabled device is integrated into the television with an Internet connection and the data is being streamed to the computer enabled device or smartphone or Internet connected television. whereas the uploading user channels can be television shows which can be established on and regional level or other level and provide advancement to a wider broadcast or larger prospective audience or wider distribution or other type of media dissemination and distribution which can be easily implemented and executed by anyone skilled in the arts of media production, broadcasting, web site development, or other mediums of any kind such as social media, crowd funding, crowd source content delivery and any other online Internet based App for fundraising campaign, individual, group, organization, business, or charity, and Apps on a mobile device or computer of any type for any applicable purpose using my novel method described herein can be improved greatly utilizing my novel method.

Thus, specific embodiments and applications of a crowd sourced content and crowd funding App using a cloud based ASP and App has been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . . and N, the text should be interpreted as requiring only one element from the group, not A plus N, or B plus N, etc.

What is claimed is:

1. An apparatus, comprising:
   a processor;
   a memory;
   a set of logics configured to dynamically expire crowd-sourced content provided to a crowd-sourced database; and
   an interface to connect the processor, the memory, and the set of logics;
   the set of logics comprising:
      a first logic configured to acquire a contribution from a user, where the contribution is data associated with the crowd-sourced content, where the data is provided by a mobile device, and where the data is configured for storage on a computer-readable storage medium and the data includes metadata identifying a location of the mobile device;
      a second logic configured to produce a geographic limit to the viewing of the contribution and voting of users on the contribution based on the metadata, the second logic configured to change the geographic limit and the metadata in response to receiving a payment notification; and
      a third logic configured to selectively update the number of user generated votes for the contribution and
      a forth logic configured to classify and group the contribution by
         a first criteria selected from a group consisting of
            its stated cause,
            charity, and
            fundraising goals,
         a status criteria,
         an expiration criteria, and
         a number of votes acquired at each level of a set of participation and expanded exposure of the content achieved by the contributor for the crowd-sourced content based on the vote rating or vote based popularity of the contribution of a specific user; and
      the expiration criteria being stored in the crowd-sourced database.

2. The apparatus of claim 1, further comprising the first logic being configured to acquire the contribution as data concerning a funding need, a charity, an investment, a contest, or other similar requirement, here the data concerning the funding need or other such petition by the contestant or uploading contributor includes a requirement to be voted yes by a user for the data to remain on the data base and or advance to a wider and or higher level of access and viewer exposure by voting the contribution up to a larger geographic viewing audience.

3. The apparatus of claim 1, the second logic being configured to produce the evaluation based on the number of votes received in an established state or regional area or geographical location, of the contributed content or data sets to the crowd-sourced database.

4. The apparatus of claim 3, the second logic being configured to selectively adapt how the evaluation is produced based on a correlation between an expiration criteria and an actual expiration.

5. The apparatus of claim 2, the third logic being configured to update the user profile based on a confirmation of the number of votes accumulated.

6. The apparatus of claim 2, comprising a fourth logic configured to selectively expire the crowd-sourced content based, at least in part, on the expiration criteria, and the number of votes accumulated.

7. The apparatus of claim 1, comprising a fourth logic configured to selectively expire the crowd-sourced content based, at least in part, on the expiration criteria, and the amount of money sought by the contestant or uploading user.

8. The apparatus of claim 1, comprising a fourth logic configured to selectively expire the crowd-sourced content based, at least in part, on the expiration criteria, where expiring the crowd-sourced content allows data in the crowd-sourced database that is associated with the crowd-sourced content to be used in evaluations of other crowd-sourced content.

9. An apparatus, comprising:
   a processor;
   a memory;
   a set of logics configured to dynamically expire crowd-sourced content provided to a crowd-sourced database; and
   an interface to connect the processor, the memory, and the set of logics;
   the set of logics comprising:
      a first logic configured to acquire a contribution from a user, where the contribution is data associated with the crowd-sourced content, where the data is provided by a mobile device, and where the data is configured for storage on a computer-readable storage medium for the purpose of a contest, the first logic assigning a first geographic range limiting the viewing range of the contribution;
      a second logic configured to produce a rating of the contribution based on votes made by users within the first geographic range; and
      a third logic configured to assign a second geographic range to the contribution in response to a received fee, the second geographic range being larger than the first geographic range and improving the odds of receiving more votes and affect the rating of the crowd-sourced content based on the vote rating or vote based popularity of the contribution of a specific user and the number of votes being stored in the crowd-sourced database.

* * * * *